United States Patent [19]

Kirst

[11] 4,360,665
[45] Nov. 23, 1982

[54] 4"-N-(SUBSTITUTED)-APRAMYCIN ANTIBIOTIC DERIVATIVES AND INTERMEDIATES THEREFOR

[75] Inventor: Herbert A. Kirst, Indianapolis, Ind.

[73] Assignee: Eli Lilly and Company, Indianapolis, Ind.

[21] Appl. No.: 334,408

[22] Filed: Dec. 24, 1981

[51] Int. Cl.³ .......................................... C07H 15/22
[52] U.S. Cl. .................................... 536/16.8; 424/180
[58] Field of Search .................. 536/17 R, 4; 424/118

[56] References Cited

U.S. PATENT DOCUMENTS 3,691,279  9/1972  Thompson et al. ................. 424/118
3,853,709  12/1974  Stark ................................... 424/118
3,876,767  4/1975  Ose ..................................... 424/118

OTHER PUBLICATIONS

O'Connor et al., "Chem. Abst.", vol. 85, 1976, p. 21,760(t).
S. Nakagawa et al., *J. Antibiotics (Tokyo)*, 31, 675 (1978).
K. Richardson et al., *J. Antibiotics (Tokyo)*, 30, 843 (1977).
A. Fujii et al., *J. Antibiotics (Tokyo)*, 21, 340 (1968).
M. B. Thomas and M. T. Williams, *Tetrahedron Lett.*, 21, 4981 (1980).
E. Akita et al., *J. Antibiotics (Tokyo)*, 26, 365 (1973).
Y. Abe et al., *J. Antibiotics (Tokyo)*, 34, 1434 (1981).

*Primary Examiner*—Johnnie R. Brown

[57] ABSTRACT

Apramycin derivatives substituted at the 4"-amino group with a variety of substituents are broad spectrum antibiotics. Also claimed are intermediates in the synthesis of these apramycin derivatives.

14 Claims, No Drawings

4''-N-(SUBSTITUTED)-APRAMYCIN ANTIBIOTIC DERIVATIVES AND INTERMEDIATES THEREFOR

BACKGROUND OF THE INVENTION

This invention relates to antibiotic derivatives of apramycin and intermediates in the synthesis therefor. In particular, it relates to apramycin derivatives in which the 4''-amino group is derivatized by a $C_2$ to $C_4$-alkyl, $C_1$ to $C_4$-acyl, benzyl, methoxybenzyl, halobenzyl, γ-amino-α-hydroxybutyryl, β-amino-α-hydroxypropionyl, glycyl, 4-amino-2-hydroxybutyl, 3-amino-2-hydroxypropyl or 2-aminoethyl group; and the pharmaceutically acceptable acid addition salts thereof.

Apramycin is used as a veterinary antibiotic (see U.S. Pat. Nos. 3,961,279, 3,853,709 and 3,876,767) and has the following structure:

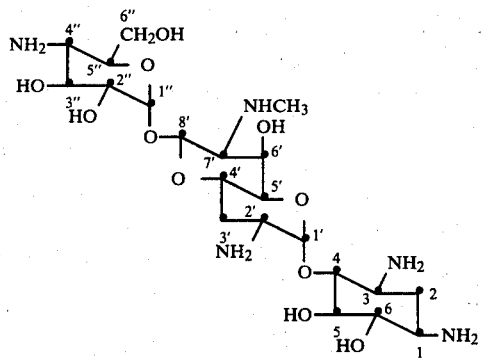

It is known in the art that substitution on various positions of the aminoglycoside rings may increase the activity of the parent aminoglycoside. Some recent substituted-apramycin derivatives, in which the 1, 3 and 2'-amino groups were derivatized, have been reported by Herbert A. Kirst, Brenda A. Truedell and John E. Toth in *Tetrahedron Letters*, vol. 22, pp 295-298 (1981).

The apramycin derivatives of the instant application are substituted at the 4''-position and possess broad-spectrum antibiotic activity while differing in structure from the aforementioned compounds and other compounds previously disclosed in the art.

SUMMARY OF THE INVENTION

The 4''-(substituted-amino)apramycin antibiotics of this invention are represented by the following formula A:

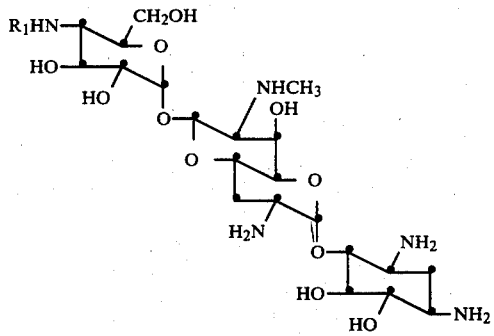

wherein $R_1$ is $C_2$ to $C_4$-alkyl, $C_1$ to $C_4$-acyl, benzyl, methoxybenzyl, halobenzyl, γ-amino-α-hydroxybutyryl, β-amino-α-hydroxypropionyl, glycyl, 4-amino-2-hydroxybutyl, 3-amino-2-hydroxypropyl or 2-aminoethyl; and the pharmaceutically acceptable acid addition salts thereof.

A second aspect of this invention provides intermediates useful in the synthesis of the above apramycin antibiotics. One group of intermediates is represented by formula B:

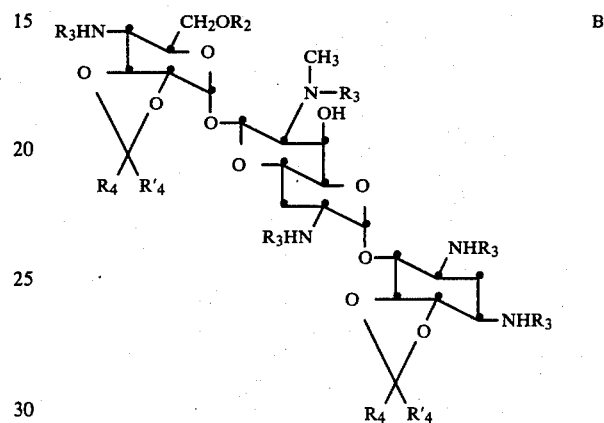

wherein $R_2$ is $C_1$ to $C_4$-acyl, γ-phthalimido-α-hydroxybutyryl, β-phthalimido-α-hydroxypropionyl or N-phthalimidoglycyl; $R_3$ is benzyloxycarbonyl and $R_4$ and $R_4'$ are each methyl or, taken together, form a cyclohexyl ring.

A second group of intermediates in the synthesis of the above 4''-N-(substituted) apramycin antibiotics is represented by the following formula C:

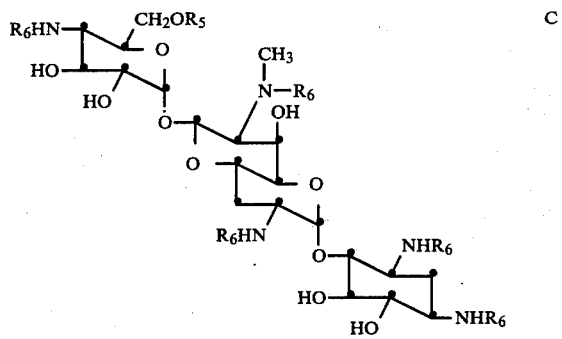

wherein $R_5$ is $C_1$ to $C_4$-acyl, γ-phthalimido-α-hydroxybutyryl, β-phthalimido-α-hydroxypropionyl or N-phthalimidoglycyl; and $R_6$ is benzyloxycarbonyl.

The third group of intermediates provided in the instant application is represented by the following formula D:

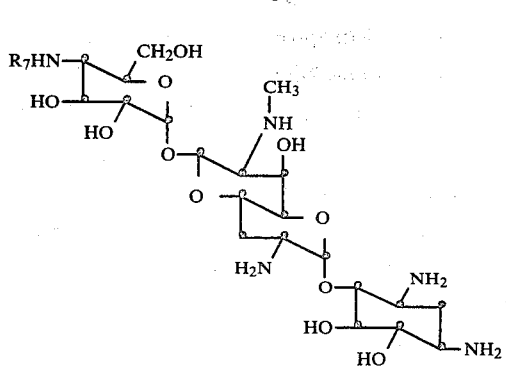

wherein R$_7$ is γ-phthalimido-α-hydroxybutyryl, β-phthalimido-α-hydroxypropionyl or N-phthalimidoglycyl.

DETAILED DESCRIPTION OF THE INVENTION

This invention is directed to certain 4''-N-(substituted)-apramycin antibiotic compounds and the intermediates for the synthesis of these antibiotics.

Specifically, this invention relates to apramycin antibiotic compound which are substituted on the 4''-amino group by a substituent chosen from the group consisting of C$_2$ to C$_4$-alkyl, C$_1$ to C$_4$-acyl, benzyl, methoxybenzyl, halobenzyl, γ-amino-α-hydroxy-butyryl, β-amino-α-hydroxypropionyl, glycyl, 4-amino-2-hydroxybutyl, 3-amino-3-hydroxypropyl, 2-aminoethyl and the pharmaceutically acceptable acid addition salts thereof.

Additionally, three groups of intermediates used in the synthesis of the above 4''-N-(substituted)apramycin antibiotic compounds are provided in the instant application. In one group of intermediates, the 1,3,2',7' and 4''-amino groups are protected with benzyloxycarbonyl (CBZ) groups, the 2'', 3'' and 5,6 pairs of hydroxyl groups are each protected with an isopropylidene group, and the 6''-hydroxyl group is acylated with a substituent chosen from the group consisting of C$_1$ to C$_4$-acyl, γ-phthalimido-α-hydroxybutyryl, β-phthalimido-α-hydroxypropionyl and N-phthalimidoglycyl.

The second group of intermediates parallels the above group of intermediates at all positions except that the 2'', 3'' and 5,6 pairs of hydroxyl groups are unprotected, that is, they exist as free hydroxyl groups.

The third group of intermediates of the present application that are used in the synthesis of the novel 4''-N-(substituted)-apramycin antibiotic compounds are apramycin derivatives wherein the 4''-amino group has been acylated with either a γ-phthalimido-α-hydroxybutyryl group, a β-phthalimido-α-hydroxypropionyl group or an N-phthalimidoglycyl group.

In the description of the invention, the term "C$_2$ to C$_4$-alkyl" means ethyl, n-propyl and n-butyl.

As used herein, the term "C$_1$ to C$_4$-acyl" means formyl, acetyl, propionyl and n-butyryl.

The term "methoxybenzyl" means ortho-methoxybenzyl, meta-methoxybenzyl or para-methoxybenzyl. Similarly, the term "halobenzyl" indicates a benzyl group substituted on the phenyl ring with one halogen atom selected from the group consisting of fluoro, chloro, bromo and iodo in either the ortho, meta or para position. Examples of such substituted benzyl groups include para-chlorobenzyl, para-bromobenzyl, para-iodobenzyl, para-fluorobenzyl, ortho-chlorobenzyl, ortho-bromobenzyl, meta-iodobenzyl, meta-fluorobenzyl and the like.

As used in the instant application, the term "pharmaceutically acceptable acid addition salts" means those formed by standard acid-base reactions between the appropriate aminoglycoside and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, salicylic, methanesulfonic, benzenesulfonic, sorbic, picric, benzoic, cinnamic and like acids.

Those skilled in the art will recognize that the γ-amino-α-hydroxybutyryl, γ-protected amino-α-hydroxybutyryl, β-amino-α-hydroxypropionyl, β-protected amino-α-hydroxypropionyl, 4-amino-2-hydroxybutyl and 3-amino-2-hydroxypropyl groups can exist as optical isomers. For the purposes of this invention, these terms refer to either the pure R or S isomers or to an equal or unequal mixture of these isomers at the asymmetric carbon atom.

The method for obtaining apramycin, the starting material in the instant invention, is described in U.S. Pat. Nos. 3,691,279 and 3,853,709, where apramycin is referred to as "nebramycin factor II". The subject matter in both U.S. Pat. Nos. 3,691,279 and 3,853,709 are herein incorporated by reference.

In the following Scheme, the term "Apra" stands for apramycin. Where the term "Apra" is not used explicitly in the terms representing the compounds in Schemes 1 and 2, it is assumed that the various substitutions are on an apramycin molecule. The symbol "o—o" indicates an isopropylidene or a cyclohexylidene hydroxy-protecting group on the 2'',3'' and 5,6 pairs of vicinal hydroxy groups. The symbol "(ester)$_4$" (or tetra-O-acyl) means that each of the 2'',3'',5 and 6 hydroxy groups are acylated by a formyl, acetyl, propionyl, n-butyryl, γ-phthalimido-α-hydroxybutyryl, β-phthalimido-α-hydroxypropionyl or an N-phthalimidoglycyl group. Similarly, the symbol "(ester)$_5$" (or penta-O-acyl) means the same as "(ester)," except that the 6''-hydroxy group is also acylated by one of the specified acyl groups listed above. The term "6''-ester" (or 6''-O-acyl) means that only the 6''-hydroxy group is acylated by one of the above-specified acyl groups. The term "4''-amide" refers to a compound wherein a formyl, acetyl, propionyl, n-butyryl, γ-amino-α-hydroxybutyryl, β-amino-α-hydroxybutyryl or glycyl group is attached to the 4''-amino group of apramycin. The term "4''-NHR" indicates that the acyl group bonded to the 4''-amino group has been reduced at the carbonyl moiety to produce the corresponding 4''-N-alkyl derivative.

The term "N$_5$" indicates that all of the amino groups of the apramycin nucleus are acylated by benzyloxycarbonyl protecting groups.

The term "Ar" indicates an unsubstituted phenyl ring or a phenyl ring monosubstituted in the ortho, meta or para position with methoxy, fluoro, chloro, bromo or iodo.

The term "[Apra·Cu]" indicates an apramycin molecule complexed with copper acetate. This complex facilitates alkylation of the 4''-amino group.

The term "R" represents the ethyl, n-propyl, n-butyl, 4-amino-2-hydroxybutyl, 3-amino-2-hydroxypropyl or 2-aminoethyl group. By R' we mean ethyl, n-propyl or n-butyl.

The method for the synthesis of the compounds claimed in the instant application is diagramed in the following Schemes (Schemes 1 and 2)

Scheme 1

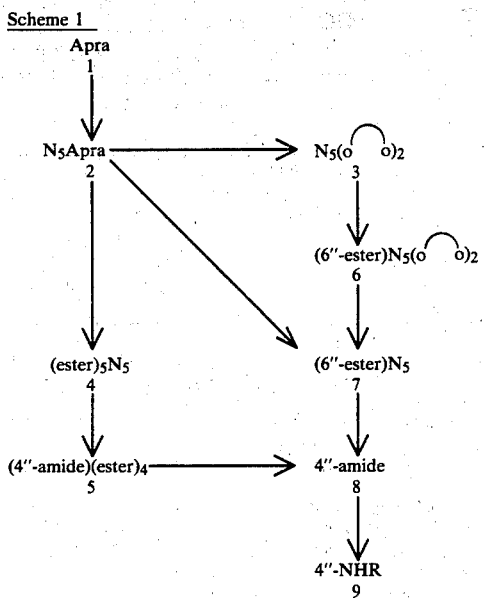

Scheme 2

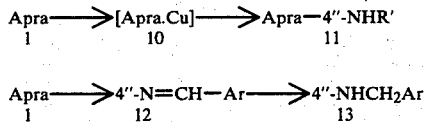

One general route to the 4''-amide apramycin antibiotics ("4''-N-acyl antibiotics" (8)) involves protecting the five amino groups of apramycin by preparing penta-N-CBZ-apramycin (2), acylating the five hydroxy groups of this penta-N-CBZ compound (2) to give a penta-N-CBZ-penta-O-acyl apramycin intermediate (4) (where acyl is preferably formyl, acetyl, propionyl or n-butyryl) and removing the five CBZ groups from (4), resulting in the migration of the 6''-ester to the newly deprotected 4''-amino group (an ester to amide rearrangement), yielding 4''-N-acyl-2'',3'',5,6-tetra-O-acyl apramycin intermediate (5). This 4''-N-acyl-tetra-O-acyl apramycin intermediate is then converted into the 4''-N-amide apramycin antibiotic compound (8).

More specifically, the 1,3,2',7',4''-penta-N-benzyloxycarbonylapramycin (2) referred to above can by synthesized by methods well known to those skilled in the aminoglycoside art. For example, penta-N-benzyloxycarbonylapramycin can be synthesized by reacting apramycin with five molar equivalents (or a slight excess) of a benzyloxycarbonyl acylating agent, represented by the following formula

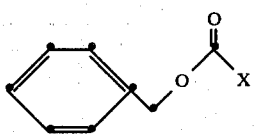

wherein X can be chloro, para-nitrophenoxy, acyloxy, N-oxysuccinimide or N-oxyphthalimide.

A preferred method of synthesizing 1,3,2',7',4''-penta-N-benzyloxycarbonylapramycin ("penta-N-CBZ apramycin" (2)) involves reacting apramycin with benzyloxycarbonyl chloride in the presence of sodium carbonate in cold aqueous acetone.

The conversion of penta-N-CBZ apramycin (2) to a penta-N-CBZ-penta-O-acyl apramycin intermediate (4) involves reacting penta-N-CBZ apramycin (2) with an anhydride or other active acylating agent, preferably a symmetrical anhydride (e.g. acetic, propionic or n-butyric anhydride) or an unsymmetrical anhydride (e.g. formic acetic anhydride) in the presence of a base such as pyridine to give the penta-N-CBZ-penta-O-acyl apramycin (4). Preferable acyl groups are formyl, acetyl, propionyl or n-butyryl.

The key step of this method involves removing the 4''-N-protecting group so that migration of the 6''-O-acyl group to the 4''-amino-group can occur. This can be accomplished by hydrogenation of the penta-N-CBZ-penta-O-acyl apramycin (4) in an aqueous organic solvent (e.g. alcohol, dioxane) over a hydrogenation catalyst such as palladium on carbon to yield the 4''-N-acyl-2'',3'',5,6-tetra-O-acylapramycin intermediate (5). The four O-acyl groups are then removed from this intermediate (5) by warming it in alcoholic hydrazine hydrate to yield the 4''-N-acyl antibiotic (8).

The second method for synthesizing the 4''-N-acyl antibiotics (8) of the instant invention begins with the conversion of penta-N-CBZ apramycin (2) to the penta-N-CBZ-2'',3'';5,6-di(ketal) apramycin (3), where "ketal" can be an isopropylidene or cyclohexylidene group. This conversion can be carried out by methods well-known to those skilled in the art, such as by methods discussed in T. W. Greene, Protective Groups in Organic Synthesis, New York, 1981, pages 72 through 86. One example of such a procedure involves treatment of penta-N-CBZ apramycin (2) in benzene-dimethylformamide solution with 2,2-dimethoxypropane and p-toluenesulfonic acid as catalyst followed by selective hydrolysis of the 6''-ketal under aqueous acidic conditions.

The penta-N-CBZ-2'',3'';5,6-(diketal)-apramycin (3) can be acylated by active acylating agents (such as anhydrides or reactive esters such as N-oxysuccinimide esters) in a base such as pyridine to yield the 6''-O-acyl-penta-N-CBZ-2'',3'';5,6-di(ketal)apramycin intermediate (6). The two ketal groups of this intermediate (6) may be removed by acid hydrolysis, according to methods well known to those skilled in the art, to yield the 6''-O-acyl-penta-N-CBZ-apramycin intermediate (7). Examples of these well known procedures can be found in T. W. Greene, ibid. pages 72–86. Alternatively, 6''-O-acyl-penta-N-CBZ-apramycin (7) can be prepared directly from penta-N-CBZ apramycin by selective acylation of the primary (6'') hydroxyl group under conditions similar to those described for acylation of the penta-N-CBZ-2'',3'';5,6-di(ketal)apramycin(3).

Finally, the 6''-O-acyl-penta-N-CBZ apramycin intermediate (7) is converted to the 4''-N-acyl apramycin antibiotic (8) by the ester to amide rearrangement described above, effected by removal of the 4''-N-benzyloxycarbonyl group under conditions for hydrogenation similar to those described for the conversion of the penta-N-CBZ-penta-O-acyl apramycin (4) to the 4''-N-acyl-tetra-O-acyl apramycin (5), supra.

The synthesis of the 4''-N-acyl antibiotic compounds, where "acyl" is glycyl, γ-amino-α-hydroxybutyryl or β-amino-α-hydroxypropionyl involves a final step of removing an N-phthalimido protecting group. The protecting group is removed by warming a solution of the phthalimido-protected 4''-N-acyl apramycin with hydrazine hydrate, yielding the deblocked 4''-N-(acyl) apramycin antibiotic (8).

The 4''-N-acyl apramycin antibiotic compounds (8) can be reduced to yield the corresponding 4''-N-alkyl derivatives (9). Representative reducing agents for this conversion are diborane, lithium aluminum hydride, and like reducing agents which may be employed in reduction of amide groups.

Certain 4''-N-alkyl apramycin antibiotics of the instant invention may also be obtained by alkylation of a complex of apramycin anc copper (II) acetate (Scheme 2). This complex (10) is formed by suspending apramycin (1) in a polar organic solvent such as dimethyl sulfoxide and treating the suspension with approximately 2.5 molar equivalents of copper (II) acetate dihydrate. This dimethyl sulfoxide solution of the apramycin-copper (II) acetate complex (10) is then treated with either ethyl iodide, n-propyl iodide or n-butyl iodide. The 4''-N-alkyl apramycin compound is then separated from the copper acetate by known techniques, such as precipitation of the copper (II) as its insoluble sulfide, by dissolving the above 4''-N-alkyl apramycin-copper (II) acetate complex in hydrochloric acid solution and bubbling hydrogen sulfide through the solution to precipitate copper sulfide. The 4''-N-alkyl apramycin is then purified by standard methods of chromatography, such as ion-exchange chromatography.

The 4''-N-(optionally substituted)benzyl apramycin antibiotic compounds (13) are obtained by reduction of the Schiff bases formed between the 4''-amino group of apramycin and the optionally substituted benzaldehyde (Scheme 2). The 4''-Schiff base intermediates (12) are synthesized from apramycin (1) by adding the appropriate optionally-substituted benzaldehyde to an aqueous solution of apramycin (1) which has been adjusted to approximately pH 7 before the addition of the aldehyde. The synthesis of the 4''-N-(optionally substituted) benzyl apramycin antibiotic (13) from the 4''-Schiff base intermediate (12) involves treating the 4''-Schiff base intermediate (12) prepared in situ with a suitable metal hydride such as sodium cyanoborohydride. The 4''-N-(optionally-substituted) benzylapramycin antibiotic (13) is then purified by standard procedures, such as chromatography on an ion-exchange resin.

The 4''-N-substituted antibiotic compounds of this invention, either in their free base form or their pharmaceutically acceptable acid addition salt form, are useful for treating infections in warm-blooded animals caused by gram-positive and gram-negative bacteria. These compounds can be administered parenterally, in the free base form or in the pharmaceutically acceptable acid addition salt form, using pharmaceutically acceptable formulations known in the art. These compounds can also be administered as veterinary compositions, such as, for example, in the feed or drinking water of farm animals to treat infections such as colibacillosis or swine dysentery.

Alternatively, these compounds can be used as surface disinfectants. Solutions containing as little as 0.1 percent by weight of the antibiotic are effective for disinfecting purposes. Such solutions, preferably also containing a detergent or other cleansing agent, are useful for disinfecting objects such as glassware, dental and surgical instruments, and surfaces such as walls, floors, and tables in areas where maintenance of sterile conditions is important, i.e. hospitals, food-preparation areas, and the like.

The antibacterial activity of the antibiotic compounds of this invention is illustrated by the following in vitro and in vivo test data obtained with representative compounds. In Tables I and II, the minimum inhibitory concentration (MIC) for representative compounds against a wide range of gram-positive and gram-negative bacteria are presented. The MIC values were obtained by the standard agar dilution test.

TABLE 1

Antibiotic Activity of 4''-N—(Substituted)-Apramycin Antibiotic Compounds vs. Gram-Positive and Gram-Negative Bacteria

| Test Organism* | Test Compound[1] Minimum Inhibitory Concentration (mcg/ml) | |
|---|---|---|
| | 1 | 2 |
| Staphylococcus aureus X1.1 | 32 | 8 |
| Staphylococcus aureus V41 | 64 | 16 |
| Staphylococcus aureus X400 | 128 | 32 |
| Staphylococcus aureus S13E | 64 | 16 |
| Staphylococcus epidermidis EPI1 | 32 | 8 |
| Staphylococcus epidermidis EPI2 | 64 | 32 |
| Streptococcus pyogenes C203 | >128 | 32 |
| Streptococcus pneumoniae Park 1 | 128 | 32 |
| Streptococcus group D X66 | >128 | >128 |
| Streptococcus group D 9960 | >128 | >128 |
| Haemophilus influenzae HOLT | 16 | 2 |
| Haemophilus influenzae R252 | 16 | 1 |
| Shigella sonnei N9 | 32 | 16 |
| Escherichia coli N10 | 32 | 16 |
| Escherichia coli EC14 | 16 | 8 |
| Escherichia coli TEM | 16 | 4 |
| Klebsiella pneumoniae X26 | 16 | 8 |
| Klebsiella pneumoniae KAE | 16 | 8 |
| Enterobacter aerogenes X68 | 16 | 8 |
| Enterobacter aerogenes C32 | 16 | 8 |
| Enterobacter aerogenes EB17 | 16 | 4 |
| Enterobacter cloacae EB5 | 32 | 16 |
| Enterobacter cloacae 265A | 32 | 8 |
| Salmonella heidelberg X514 | 32 | 16 |
| Salmonella typhimurium 1335 | 32 | 16 |
| Pseudomonas aeruginosa X528 | 64 | 32 |
| Pseudomonas aeruginosa X239 | 64 | 16 |
| Pseudomonas aeruginosa Ps18 | 16 | 4 |
| Serratia marcescens X99 | 16 | 8 |
| Serratia marcescens SE3 | 32 | 16 |
| Proteus morganii PR15 | 32 | 16 |
| Proteus inconstans PR33 | 16 | 4 |
| Proteus rettgeri PR7 | 32 | 8 |
| Proteus rettgeri C24 | 32 | 8 |
| Citrobacter freundii CF17 | 32 | 16 |
| Bordetella bronchiseptica 16 | 128 | 32 |

*Numerals and letters following the names of test microorganisms refer to the strains.
[1]Test compounds numbered 1 and 2 are as follows:
1 = 4''-N—acetylapramycin
2 = 4''-N—ethylapramycin

TABLE II

Antibiotic Activity of 4''-N—(Substituted)-Apramycin Antibiotic Compounds vs. Gram-Negative Bacteria

| Test Organism* | Test Compound[1] Minimum Inhibitory Concentration (mcg/ml) | | |
|---|---|---|---|
| | 1 | 2 | 3 |
| Klebsiella pneumoniae KL2 | 8 | 4 | 8 |
| Enterobacter aerogenes EB6 | 8 | 2 | 8 |
| Enterobacter cloacae EN453 | 8 | 4 | 8 |
| Enterobacter cloacae EB24 | 8 | 4 | 4 |
| Pseudomonas aeruginosa X48 | 32 | — | >128 |
| Pseudomonas aeruginosa X528 | 64 | 32 | >128 |
| Pseudomonas aeruginosa X239 | 32 | 16 | 128 |
| Pseudomonas aeruginosa Ps9 | 128 | 64 | >128 |
| Pseudomonas aeruginosa Ps15 | 32 | 16 | 128 |
| Pseudomonas aeruginosa Ps25 | 32 | 16 | 64 |
| Pseudomonas aeruginosa 4276 | 32 | 8 | >128 |
| Pseudomonas aeruginosa PI23 | >128 | >128 | >128 |

TABLE II-continued

Antibiotic Activity of 4″-N—(Substituted)-Apramycin Antibiotic Compounds vs. Gram-Negative Bacteria

| Test Organism* | Test Compound[1] Minimum Inhibitory Concentration (mcg/ml) | | |
|---|---|---|---|
| | 1 | 2 | 3 |
| Pseudomonas aeruginosa SF-2 | 64 | 16 | 128 |
| Serratia marcescens SE2 | 8 | 4 | 16 |
| Serratia marcescens X99 | 4 | 2 | 4 |
| Serratia marcescens SE3 | 8 | 4 | 8 |
| Proteus morganii PR1 | 8 | 4 | 32 |
| Proteus rettgeri PR2 | 32 | 8 | >128 |
| Proteus inconstans PV25 | 8 | 4 | 64 |

*Numerals and letters following the names of test microorganisms refer to the strains.
[1]Test compounds numbered 1–3 are as follows:
1 = 4″-N—acetylapramycin
2 = 4″-N—ethylapramycin
3 = 4″-N—benzylapramycin Table III illustrates the effective dose ($ED_{50}$, effective dose to protect 50 percent of the test animals) for a representative compound of this invention against an experimental bacterial infection in mice.

TABLE III

Subcutaneous Therapy of Staphlyococcus aureus 3055 Infections in Mice

| Test Compound | Effective Dose ($ED_{50}$)* |
|---|---|
| 4″-N—Acetylapramycin | 9.4 |

*mg/kg × 2 subcutaneous doses at 1 and 5 hours post-infection

The $ED_{50}$ value was determined as described by W. E. Wick et al., *Journal of Bacteriology*, 81 [No. 2], 233–235 (1961).

The following Examples (1 through 4) are provided to further illustrate this invention. Preparations 1 and 2 provide N- and N and O-protected apramycin starting materials for the synthesis of the claimed 4″-N-substituted apramycin intermediate and antibiotic compounds. Preparation 3 provides an example of the synthesis of an activated ester acylating agent used in the synthesis of the compounds of the instant invention. It is not intended that this invention be limited in scope by reason of any of the Preparations or Examples.

In the following Preparations and Examples, carbon-13 nuclear magnetic resonance, field desorption mass spectra and high performance liquid chromatography are abbreviated C-13 n.m.r., f.d.m.s. and HPLC, respectively. The nuclear magnetic resonance spectra were obtained on either a Varian Associates FT-80 Spectrometer or a JEOL JNM-PS-100 Spectrometer using dioxane as the internal standard. The chemical shifts are expressed in δ values (parts per million downfield from tetramethylsilane). The term "pyridine-$d_5$" stands for perdeuteriopyridine. The field desorption mass spectra were taken on a Varian-MAT 731 Spectrometer using carbon dendrite emitters. High performance liquid chromatography was carried out on a Waters Associates, Inc. Prep 500 instrument.

Column chromatography was often carried out using an ion exchange resin such as Bio-Rex 70 as the stationary phase. Bio-Rex 70 is a weakly acidic cation exchange resin containing carboxylic acid groups on a macroreticular acrylic polymer lattice and is a product of Bio-Rad Labs, 2200 Wright Ave., Richmond, Ca. 94804. Thin layer chromatography was carried out on E. Merck silica gel plates.

The abbreviations mmol and h stand for millimole and hour, respectively.

In the following Examples and Preparations the term "Penta-N-CBZ" sometimes appears in compound names. This term is an abbreviated form for "1,3,2′,7′,4″-penta-N-benzyloxycarbonyl".

PREPARATION 1

1,3,2′,7′4″-Penta-N-CBZ-Apramycin

Apramycin (27 g, 50 mmol) was dissolved in water (250 ml) and the solution was diluted with acetone (250 ml), treated with sodium carbonate (26.5 g, 250 mmol) and cooled in an ice bath. Benzyloxycarbonyl chloride (51.3 g, 300 mmol) was added dropwise with vigorous mechanical stirring. After stirring for 1 h in the ice bath and 2.5 h at room temperature, the reaction mixture was extracted with ethyl acetate. The organic extracts were washed with saturated sodium chloride solution, dried over magnesium sulfate and filtered and the filtrate was evaporated under reduced pressure. The resultant residue was dried at 40° C. in vacuo to give 61.0 g (100%) of 1,3,2′,7′,4″-penta-N-CBZ-apramycin.

C-13 n.m.r. (pyridine-$d_5$) δ31.0, 33.1, 36.0, 51.6 (x2), 52.8, 55.3, 59.3, 63.0, 66.4–67.0, 70.9, 71.9, 74.0, 74.8, 76.7, 78.4, 84.6, 95.7, 98.2, 100.4, 127.1–129.7, 137.5–138.7, 156.7–158.3; f.d.m.s. m/e=1210 (P+1).

PREPARATION 2

1,3,2′,7′,4″-Penta-N-CBZ-2″,3″; 5,6-tetra-O-Diisopropylidene-Apramycin

Penta-N-CBZ-apramycin (50 g, 41.3 mmol) was dissolved in benzene (800 mmol)-dimethylformamide (120 ml) and then treated with 2,2-dimethoxypropane (100 ml) and p-toluenesulfonic acid monohydrate (1.5 g). The solution was refluxed with slow removal of all volatiles (300 ml/7 h); a solution of dimethoxypropane (12 ml) in benzene (100 ml) was added after 2 h and after 4 h in order to replenish the reagent and the solvent.

After 7 h, the solution was cooled, diluted with ethyl acetate (400 ml) and extracted with saturated sodium bicarbonate solution (200 ml). The organic solution was separated, dried over sodium sulfate/potassium carbonate and filtered and the filtrate was evaporated under reduced pressure. The residue (60 g) was dissolved in methanol (800 ml)-water (150 ml) and then treated with glacial acetic acid (10 ml). After 6 h at room temperature, the mixture was made basic with 5 M sodium hydroxide solution and concentrated to aqueous under reduced pressure, yielding a precipitate. Chloroform (500 ml) was added to dissolve the precipitate and the chloroform layer was separated, extracted with saturated sodium bicarbonate solution (150 ml), dried over sodium sulfate/potassium carbonate and filtered. The filtrate was evaporated under reduced pressure and the crude product obtained (54 g) was divided into 3 portions, each of which was chromatographed by HPLC on silica gel (Waters Prep 500 Instrument); the samples were loaded on the column in dichloromethane solution and eluted with a linear gradient of 2% ethanol in dichloromethane (4 l) and 6% ethanol in dichloromethane (4 l). Fractions containing the desired product were located by thin layer chromatography analysis, and these fractions were combined and evaporated under reduced pressure to yield 26.4 g (50%) of 1,3,2′,7′,4″-penta-N-CBZ-2″; 5,6-tetra-O-diisopropylidene-apramycin:

C-13 n.m.r. (pyridine-d₅) δ26.5–27.0, 30.7, 33.0, 37.0, 49.8, 50.4, 51.7, 54.0, 59.0, 62.7, 66.3–67.0, 71.0, 74.3, 76.6, 77.2, 78.2, 79.4, 81.8, 93.8, 94.6, 96.7, 110.7, 111.5, 127.8–128.8, 137.4–139.1, 156.5–157.4.

PREPARATION 3

N-(S-γ-Phthalimido-α-Hydroxybutyryloxy)Succinimide

S-γ-Phthalimido-α-hydroxybutyric acid (4.98 g, 20 mmol) and N-hydroxysuccinimide (2.30 g, 20 mmol) were dissolved in dimethylformamide (150 ml), and this solution was cooled in an ice bath and treated with dicyclohexylcarbodiimide (4.5 g, 22 mmol). After stirring this reaction mixture for 48 hours at room temperature, the precipitate that had formed was removed by filtration and the filtrate was evaporated under reduced pressure. The resultant residue was triturated with 2:1 Skelly B:benzene, and the insoluble product was isolated by filtration, washed again with Skelly B:benzene (2:1) and allowed to dry to yield 7.33 g of the desired product, N-(S-γ-phthalimido-α-hydroxybutyryloxy)-succinimide.

EXAMPLE 1

4″-N-Ethylapramycin

To a suspension of apramycin (1.6 g, 3.1 mmol) in dimethylsulfoxide (75 ml) was added copper (II) acetate dihydrate (1.5 g, 7.6 mmol), and the mixture was stirred for 1 h at room temperature to yield a green solution. Ethyl iodide (3.8 ml, 24.4 mmol) was added dropwise and the solution was stirred overnight at room temperature. The reaction mixture was poured into ethyl acetate (600 ml) and again stirred overnight. Solvent was decanted from the resultant oil and the oil was triturated twice more with ethyl acetate (2×600 ml), yielding a solid precipitate on the final treatment with ethyl acetate. The precipitate was collected by filtration, washed with ethyl acetate and air-dried to give the crude product-copper acetate mixture (3.51 g).

The crude product-copper acetate mixture (1.94 g) was dissolved in 0.1 N hydrochloric acid (20 ml) and diluted with methanol (20 ml). Hydrogen sulfide gas was bubbled over a 20 minute period into the stirred mixture. After the mixture had stood for 0.5 h, the precipitate was removed by filtration using Celite and the filtrate was evaporated under reduced pressure to give crude 4″-N-ethylapramycin (1.59 g). A portion of the crude 4″-N-ethylapramycin (1.04 g) was dissolved in water (15 ml), the resulting solution's pH was adjusted to 9.7 with 1 N sodium hydroxide solution, and the solution was loaded on a column of Bio-Rex 70 (NH₄⁺ cycle, pH 9.5). The column was eluted with a linear gradient of 0.01 N ammonium hydroxide solution (1 liter) and 0.1 N ammonium hydroxide solution (1 liter). Fractions were analyzed by thin layer chromatography and appropriate fractions were combined and lyophilized to yield the desired compound, 4″-N-ethylapramycin (38 mg), along with 3-N-ethylapramycin (384 mg) and 3,4″-di-N-ethylapramycin (60 mg). 4″-N-ethylapramycin: C-13 n.m.r. (H₂O-D₂O, pH 9–11) δ15.1, 32.8, 33.2, 36.6, 43.3, 49.8, 50.3, 51.2, 59.7, 61.9, 62.3, 66.6, 67.9, 71.0, 71.8, 72.2, 73.4, 76.8, 78.5, 87.8, 95.1, 96.5, 101.6.

EXAMPLE 2

4″-N-Benzylapramycin

Apramycin (539 mg, 1 mmol) was dissolved in water (100 ml), and this solution's pH was adjusted to 7.0 with aqueous hydrochloric acid and then treated with benzaldehyde (1.06 ml, 10 mmol). The mixture became homogeneous within 0.25 h and was stirred for 5.5 h at room temperature. The solution was cooled in an ice bath and treated with sodium cyanoborohydride (32 mg, 0.5 mmol). After stirring overnight, the mixture was diluted with methanol and then evaporated to dryness under reduced pressure to give crude 4″-N-benzylapramycin (5.7 g).

The crude 4″-N-benzylapramycin was dissolved in water (5 ml), the solution's pH was adjusted to 9.5 and the solution was loaded on a column of Bio-Rex 70 (150 ml, NH₄⁺ cycle, pH 9.5). The column was eluted with a linear gradient of water (1 liter) and 0.2 N ammonium hydroxide solution (1 liter). Fractions were analyzed by thin layer chromatography and appropriate fractions were combined and lyophilized to yield the desired compound, 4″-N-benzylapramycin (19 mg), and 3-N-benzylapramycin (130 mg). 4″-N-benzylapramycin: C-13 n.m.r. (H₂O-D₂O, pH 9–11) δ32.5, 33.0, 35.7, 49.7, 50.2, 51.2, 52.9, 59.3, 62.0, 62.3, 66.3, 67.8, 71.0, 72.0 (x2), 73.4, 76.7, 77.5, 87.2, 95.1, 96.5, 101.2, 128.4, 129.6, 140.0.

EXAMPLE 3

4″-N-Acetylapramycin

A solution of penta-N-CBZ-apramycin (5.4 g, 4.46 mmol) dissolved in pyridine (250 ml) was cooled in an ice bath and treated dropwise with acetic anhydride (10 ml). As the solution was stirred overnight, it was allowed to warm to room temperature. The solution was evaporated to dryness under reduced pressure and the resultant residue was dissolved in ethyl acetate (200 ml). This solution was extracted with saturated sodium bicarbonate solution (100 ml) and the organic layer was separated, dried over sodium sulfate-potassium carbonate and filtered. The filtrate was evaporated to dryness, the residue (6.3 g) was dissolved in ethanol (175 ml) and the solution was diluted with water (25 ml). The solution was hydrogenated (1 atm H₂) over 5% palladium/carbon (6 g) overnight at room temperature. The catalyst was removed by filtration and the filtrate was evaporated to dryness. The residue (2.7 g) was dissolved in 95% ethanol (200 ml) and hydrazine hydrate (8 ml) and the resultant solution was refluxed for 1 h. The solution was cooled to room temperature and then evaporated to dryness. The resultant residue was dissolved in water (20 ml, pH 8.9) and loaded onto a column of Bio-Rex 70 (650 ml, NH₄³⁰ cycle, pre-eluted with 0.005 N ammonium hydroxide solution). The column was eluted with 0.005 N ammonium hydroxide solution (2 l) followed by a linear gradient composed of of 0.005 N ammonium hydroxide solution (2 l) and 0.064 N ammonium hydroxide solution (2 l) and finally eluted with an additional amount of 0.064 N ammonium hydroxide solution (2 l). Fractions were analyzed by thin layer chromatography and appropriate fractions were combined and lyophilized to yield the desired product, 4″-N-acetylapramycin (762 mg, 29%). From fractions collected earlier in the chromatography, 4″,7′-di-N-acetylapramycin (379 mg, 13%) was obtained. 4″-N-acetylapramycin:

C—13 n.m.r. (H$_2$O-D$_2$O, pH 9–11) δ23.2, 33.0 (x2), 36.9, 49.9, 50.4, 52.5, 61.8, 62.4, 66.1, 67.9, 71.1, 71.4, 72.4, 72.5, 77.4, 78.7, 88.0, 95.5, 96.4, 101.6, 175.3.

EXAMPLE 4

4''-N-(S-γ-Amino-α-Hydroxybutyryl)-Apramycin

Step A: Preparation of Penta-N-CBZ-2'',3''; 5,6-Tetra-O-Diisopropylidene-6''-O-(γ-Phthalimido-α-hydroxybutyryl)apramycin 2'',3'';5,6-Tetra-O-diisopropylidene-penta-N-CBZ-apramycin (2.58 g, 2 mmol) was dissolved in pyridine (20 ml), and this solution was cooled in an ice bath and treated with N-(S-γ-phthalimido-α-hydroxybutyryloxy)-succinimide (3.46 g, 10 mmol). The reaction mixture was stirred at room temperature for 12 days. The solvent was then evaporated under reduced pressure, and the resultant oil was redissolved in chloroform. The solution was diluted with cyclohexane and re-evaporated, repeating this step if necessary in order to obtain a solid product. The residue was taken up in ethyl acetate (100 ml) and the solution was extracted with saturated sodium bicarbonate solution (2×100 ml) and saturated sodium chloride solution (100 ml). The organic layer was separated, dried over sodium sulfate/potassium carbonate and filtered, and the filtrate was evaporated under reduced pressure.

Step B: Preparation of Penta-N-CBZ-6''-O-(γ-Phthalimido-α-Hydroxybutyryl)apramycin.

The penta-N-CBZ-diisopropylidene-6''-O-substituted compound synthesized in Step A was dissolved in cold 9:1 trifluoroacetic acid-water (50 ml) and the solution was kept at 0° C. for 1 hour. The solvent was then evaporated from this solution under reduced pressure, and the residue was dissolved in ethyl acetate (50 ml) and extracted with saturated sodium bicarbonate solution (50, 25 ml) and then saturated sodium chloride solution (25 ml). The organic layer was separated, dried over sodium sulfate/potassium carbonate and filtered. The filtrate was evaporated to dryness.

Step C: Preparation of 4''-N-(γ-Phthalimido-α-Hydroxybutyryl)apramycin.

The penta-N-CBZ-6''-O-substituted compound synthesized in Step B was dissolved in ethanol (60 ml). The solution was diluted with water (15 ml) and 0.1 N hydrochloric acid (1 ml) and hydrogenated (1 atm. H$_2$) over 5% palladium/carbon (1.2 g) overnight at room temperature. The catalyst was removed by filtration, and the filtrate was evaporated to dryness.

Step D: Preparation of Final Product

The 4''-N-(γ-Phthalimido-α-hydroxybutyryl)apramycin compound synthesized in Step C was dissolved in ethanol (50 ml)-85% hydrazine hydrate (5 ml) and refluxed for 4 hours. The reaction solution was cooled, concentrated under reduced pressure, diluted with water and lyophilized. The residue was dissolved in 0.01 N ammonium hydroxide (10 ml) and loaded on a column of BioRex 70 (25 ml, NH$_4$+ cycle, pH 10) packed in 0.01 N ammonium hydroxide. The column was eluted with 0.01 N ammonium hydroxide (300 ml) and 0.1 N ammonium hydroxide (150 ml) and then with a linear gradient of 0.1 N ammonium hydroxide (500 ml) and 0.2 N ammonium hydroxide (500 ml). Fractions containing the desired product were located by thin layer chromatography analysis, combined and lyophilized to yield 22 mg of the desired product, 4''-N-(S-γ-amino-α-hydroxybutyryl)apramycin:fdms m/e=624 (P+).

I claim:

1. A compound of the formula

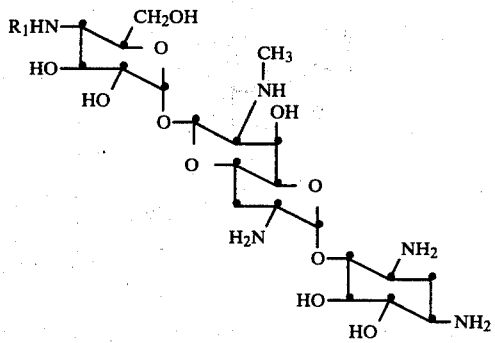

wherein R$_1$ is C$_2$ to C$_4$-alkyl, C$_1$ to C$_4$-acyl, benzyl, methoxybenzyl, halobenzyl, γ-amino-α-hydroxybutyryl, β-amino-α-hydroxypropionyl, glycyl, 4-amino-2-hydroxybutyl, 3-amino-2-hydroxypropyl or 2-aminoetyl; and the pharmaceutically acceptable acid addition salts thereof.

2. A compound of claim 1, wherein R$_1$ is C$_2$ to C$_4$-alkyl.

3. The compound of claim 2, wherein R$_1$ is ethyl.

4. The compound of claim 1, wherein R$_1$ is benzyl.

5. A compound of claim 1, wherein R$_1$ is C$_1$ to C$_4$-acyl.

6. The compound of claim 5, wherein R$_1$ is acetyl.

7. The compound of claim 1, wherein R$_1$ is γ-amino-α-hydroxybutyryl.

8. A compound of the formula

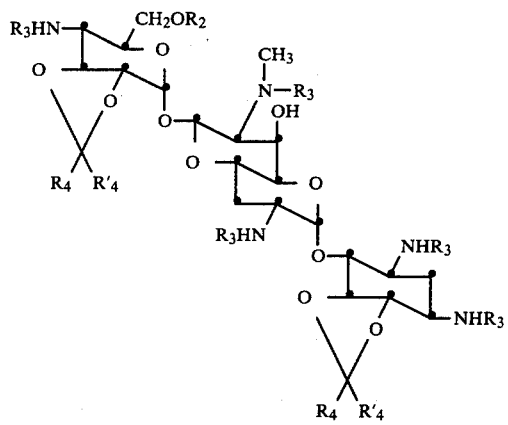

wherein

R$_2$ is C$_1$ to C$_4$-acyl, γ-phthalimido-α-hydroxybutyryl, β-phthalimido-α-hydroxypropionyl or N-phthalimidoglycyl;

R$_3$ is benzyloxycarbonyl and

R$_4$ and R$_4$' are each methyl, or, taken together form a cyclohexyl ring.

9. A compound of claim 8, wherein R$_2$ is γ-phthalimido-α-hydroxybutyryl.

10. The compound of claim 9, wherein R$_4$ and R$_4$' are each methyl.

11. A compound of the formula

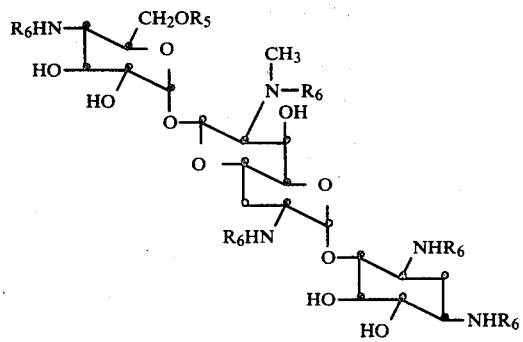

wherein $R_5$ is $C_1$-$C_4$-acyl, γ-phthalimido-α-hydroxybutyryl, β-phthalimido-α-hydrxypropionyl or N-phthalimidoglycyl; and $R_6$ is benzyloxycarbonyl.

12. The compound of claim 11, wherein $R_5$ is γ-phthalimido-α-hydroxybutyryl.

13. A compound of the formula

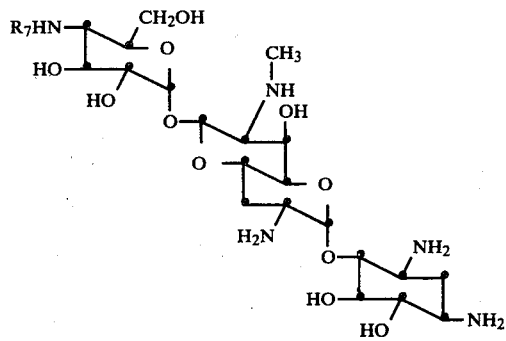

wherein $R_7$ is γ-phthalimido-α-hydroxybutyryl, β-phthalimido-α-hydroxypropionyl or N-phthalimidoglycyl.

14. The compound of claim 13, wherein $R_7$ is γ-phthalimido-α-hydroxybutyryl.

* * * * *